United States Patent
Heppenstall et al.

(10) Patent No.: US 11,834,713 B2
(45) Date of Patent: *Dec. 5, 2023

(54) INHIBITORS OF ALPHA-TUBULIN ACETYLATION FOR THE TREATMENT OF PAIN

(71) Applicant: EUROPEAN MOLECULAR BIOLOGY LABORATORY, Heidelberg (DE)

(72) Inventors: Paul Heppenstall, Monterotondo (IT); Shane Morley, Monterotondo (IT)

(73) Assignee: EUROPEAN MOLECULAR BIOLOGY LABORATORY, Heidelberg (DE)

( * ) Notice: Subject to any disclaimer, the term of this patent is extended or adjusted under 35 U.S.C. 154(b) by 203 days.

This patent is subject to a terminal disclaimer.

(21) Appl. No.: 17/383,975

(22) Filed: Jul. 23, 2021

(65) Prior Publication Data

US 2022/0002801 A1  Jan. 6, 2022

Related U.S. Application Data

(63) Continuation of application No. 16/069,818, filed as application No. PCT/EP2016/082765 on Dec. 28, 2016, now Pat. No. 11,104,949.

(30) Foreign Application Priority Data

Jan. 14, 2016  (EP) ..................................... 16151345

(51) Int. Cl.
  *C12Q 1/6886* (2018.01)
  *C12Q 1/6876* (2018.01)
  *A01K 67/027* (2006.01)
  *G01N 33/573* (2006.01)

(52) U.S. Cl.
  CPC ........ *C12Q 1/6876* (2013.01); *A01K 67/0276* (2013.01); *G01N 33/573* (2013.01); *A01K 2217/075* (2013.01); *A01K 2217/206* (2013.01); *A01K 2227/105* (2013.01); *A01K 2267/0356* (2013.01); *C12Q 2600/136* (2013.01); *C12Q 2600/158* (2013.01); *G01N 2333/91051* (2013.01)

(58) Field of Classification Search
  CPC .................................................... C12Q 1/6876
  USPC ...................................................... 424/158.1
  See application file for complete search history.

(56) References Cited

U.S. PATENT DOCUMENTS 11,104,949 B2 * 8/2021 Heppenstall ............ A61P 43/00
2014/0248635 A1   9/2014 Gaertig et al.

FOREIGN PATENT DOCUMENTS

WO   WO 2011/133559 A2   10/2011

OTHER PUBLICATIONS

Akella et al., "MEC-17 is an [alpha]-tubulin acetyltransferase", Nature, vol. 467, No. 7312, pp. 218-222, Sep. 9, 2010.
Bhuwania, R., et al., "Microtubule acetylation regulates dynamics of KIF1C-powered vesicles and contact of microtubule plus ends with podosomes," European Journal of Cell Biology, 93, 424-437 (2014).
Hu, J. and Lewin, G.R., "Mechanosensitive currents in the neurites of cultured mouse sensory neurones," The Journal of Physiology, 577, 815-828 (2006).
International Search Report and Written Opinion, International Patent Application No. PCT/EP2016/082765, dated Feb. 28, 2017 (15 pages).
Kalebic et al., "[alpha]TAT1 is the major [alpha]-tubulin acetyltransferase in mice", Nature Communications, vol. 4, pp. 1-10, Jun. 10, 2013.
Kalebic et al., "Tubulin Acetyltransferase aTAT1 Destabilizes Microtubules, Independently of Its Acetylation Activity", Molecular and Cellular Biology, vol. 33, No. 6, pp. 1114-1123, Mar. 15, 2013.
Li et al., "Tubulin acetylation: responsible enzymes, biological functions and human diseases", CMLS Cellular and Molecular Life Sciences, vol. 72, No. 22, pp. 4237-4255, Jul. 31, 2015.
Li, L et al., "MEC-17 Deficiency Leads to reduced α-tubulin acetylation and impaired migration of cortical neurons," The Journal of Neuroscience, 32, 12673-12683 (2012).
Ly, N. et al., "αTAT1 controls longitudinal spreading of acetylation marks from open microtubules extremities," Scientific Reports 6, 35624, ten pages (2016).
Mai et al., Small-Molecule Inhibitors of Histone Acetyltransferase Activity: Identification and Biological Properties, 2006, J. Med. Chem. 49:6897-6907 (Year: 2006).
Shah, N. et al., "TAK1 activation of alpha-TAT1 and microtubule hyperacetylation control AKT signaling and cell growth," Nature communications 9:1696, pp. 1-12 (2018).

(Continued)

Primary Examiner — Sean E Aeder
(74) Attorney, Agent, or Firm — Fenwick & West LLP

(57) ABSTRACT

The present invention pertains to novel analgesics useful for treating mechanical pain. The invention suggests the use of inhibitors of α-tubulin acetylation for inhibition of neurological sensations that are mediated by sensory neurons. The perception of mechanical pain is can be modulated by altering the α-tubulin acetylation, in context of the invention in particular by modulation of the expression and/or activity of the enzyme α-tubulin acetyltransferase (Atat). The invention provides the medical application of α-tubulin acetyltransferase inhibitors as analgesics and a screening method for the identification of compounds useful in the treatment of pain.

22 Claims, 4 Drawing Sheets
(4 of 4 Drawing Sheet(s) Filed in Color)

(56) References Cited

OTHER PUBLICATIONS

Shida et al., "The major (alpha]-tubulin K40 acetyltransferase aTAT1 promotes rapid ciliogenesis and efficient mechanosensation" Proceedings of the National Academy of Sciences, vol. 107, No. 50, p. 21517-21522.

Tropalidou et al., "Genetically Separable Functions of the MEC-17 Tubulin Acetyltransferase Affect Microtubule Organization", Current Biology, Current Science, vol. 22, No. 12, pp. 1057-1065, Mar. 19, 2012.

International Preliminary Report on Patentability, Chapter I, International Patent Application No. PCT/EP2016/082765, dated Jul. 17, 2018, 9 pages.

* cited by examiner

INHIBITORS OF ALPHA-TUBULIN ACETYLATION FOR THE TREATMENT OF PAIN

CROSS-REFERENCE TO RELATED APPLICATIONS

This application is a continuation of U.S. application Ser. No. 16/069,818, now granted as U.S. Pat. No. 11,104,949, filed Jul. 12, 2018, which is the National Stage under 35 USC § 371 of International Application No. PCT/EP2016/082765, filed Dec. 28, 2016, which claims priority to European Application No. 16151345.2, filed Jan. 14, 2016.

FIELD OF THE INVENTION

The present invention pertains to novel analgesics useful for treating mechanical pain. The invention suggests the use of inhibitors of α-tubulin acetylation for inhibition of neurological sensations that are mediated by sensory neurons. The perception of mechanical pain is can be modulated by altering the α-tubulin acetylation, in context of the invention in particular by modulation of the expression and/or activity of the enzyme α-tubulin acetyltransferase (Atat). The invention provides the medical application of α-tubulin acetyltransferase inhibitors as analgesics and a screening method for the identification of compounds useful in the treatment of pain.

DESCRIPTION

Pain is a complex subjective sensation reflecting real or potential tissue damage and the affective response to it. Acute pain is a physiological signal indicating a potential or actual injury. Chronic pain can either be somatogenetic (organic) or psychogenic. Chronic pain is frequently accompanied or followed by vegetative signs, which often result in depression. Chronic pain results in individual suffering and social economic costs of tremendous extent. Existing pharmacological pain therapies are widely unsatisfying both in terms of efficacy and of safety. Somatogenetic pain may be of nociceptive origin, inflammatory or neuropathic. Nociceptive pain is judged to be commensurate with ongoing activation of somatic or visceral pain-sensitive nerve fibers. Neuropathic pain results from dysfunction in the nervous system that is sustained by aberrant somatosensory processes in the peripheral nervous system.

Neuropathic pain is a persistent or chronic pain syndrome that can result from damage to the nervous system, the peripheral nerves, the dorsal root ganglion, dorsal root, or to the central nervous system. Neuropathic pain syndromes include allodynia, various neuralgias such as post herpetic neuralgia and trigeminal neuralgia, phantom pain, and complex regional pain syndromes, such as reflex sympathetic dystrophy and causalgia. Causalgia is often characterized by spontaneous burning pain combined with hyperalgesia and allodynia. Tragically there is no existing method for adequately, predictably and specifically treating established neuropathic pain as present treatment methods for neuropathic pain consists of merely trying to help the patient cope through psychological or occupational therapy, rather than by reducing or eliminating the pain experienced. Treatment of neuropathic or chronic pain is a challenge for physicians and patients since there are no medications that specifically target the condition, and since the medications presently used result in only little relief and are based on their efficacy in acute pain conditions or on their efficacy on relieving secondary effects like anxiety and depression. Incidence of chronic pain is increasing in society and its burden on society is huge in both health care and lost productivity. Currently there are no scientifically validated therapies for relieving chronic pain. As a result, the health community targets 'pain management' where multi-modal therapies are used concurrently with the hope of providing some improvement in quality of life. Thus, there is an urgent need for drugs that can relieve chronic pain.

Pain is often caused by mechanical stimuli. Mechanical forces acting upon cells or tissues can be propagated into the opening of mechanically gated ion channels either through direct interplay of ion channels with the lipid bilayer or through further interaction with other cellular components such as the underlying cytoskeleton. The bacterial mechanosensitive channel MscS7 and eukaryotic two-pore-domain potassium channels TRAAK and TREK18 are fully activated by mechanical stimuli when reconstituted in reduced membrane systems indicating that their mechanosensitivity is a result of interactions with the plasma membrane. However, from in vivo experiments carried out in eukaryotes there is evidence that mechanotransduction depends on further cellular components to amplify and shape mechanical sensitivity.

Hence, until this day there is no specific therapy for mechanical pain available. The present invention seeks to provide novel analgesics that address problems of state of the art pain treatments, such as highly toxic side effects, and particularly target pain sensation induced by mechanical stimuli.

The above problem is solved in a first aspect by an inhibitor of α-tubulin acetylation for use in the inhibition of a neurological sensation in a subject, wherein the neurological sensation is mediated by sensory neurons.

As used herein, the term "sensory neurons" relates to neurons configured to transmit neural stimuli corresponding to sensory stimuli. According to some embodiments, sensory neurons are activated by physical and/or chemical stimuli, such as, but not limited to, mechano-sensors and/or chemo-receptors. Preferred are sensory neurons which are dorsal root ganglion (DRG) neurons.

As used herein, the term "acetylation" refers to an enzymatic transfer of acetyl groups from donor molecules (e.g., acetyl CoA) to specific target substrates. In context of the present invention the preferred target molecule of the enzymatic transfer is tubulin, more preferably α-tubulin. Acetylation of the ε-amino group of lysine 40 on α-tubulin is a conserved post translational modification on the luminal side of microtubules (Nogales et al., 1999 Cell 96:79-88) that was discovered in the flagella of *Chlamydomonas reinhardtii* (L'Hernault and Rosenbaum, 1983 J. Cell Biol. 97:258-263; LeDizet and Piperno, 1987 Proc. Natl. Acad. Sci. USA 84:5720-5724). Studies on the significance of microtubule acetylation have been limited so far.

In context of the present invention it was surprisingly shown that deletion of Atat1, the main enzyme responsible for α-tubulin acetylation in mammals, from peripheral sensory neurons results in a profound and remarkably selective loss on mechanical sensation in mice. The inventors demonstrate that this impacts upon both light touch and pain, and that all mechano-receptor subtypes which innervate the skin are less responsive in the absence of α-tubulin acetylation. The inventors propose that this phenotype is caused by an increased mechanical stiffness of sensory neurons that is in turn mediated by the loss of a sub-membrane band of acetylated α-tubulin in Atat1$^{cKO}$ mice. Modulation of α-tubulin acetylation in neuronal cells is therefore a new approach to modify the sensation of tactile and pain stimuli, and other mechanically induced perceptions.

The term "neurological sensation" in context of the invention has to be understood to refer to any perception of in particular mechanical stimuli by an animal or human, most preferably tactile sensations (touch) and/or pain. Further included is the identical perception that occurs without the presence of a mechanical stimulus in the event of a for example pathologic chronic perception of the neurological sensation—such as chronic pain. Preferably the neurological sensation is mediated by peripheral sensory neurons, most preferably which are DRG peripheral sensory neurons.

The term "pain" as used herein refers to an unpleasant sensation. For example, the subject experiences discomfort, distress or suffering. It is known to one skilled in the art that various painful conditions may be classified according to broadly opposing or otherwise useful categories. Examples of opposing categories include; nociceptive pain versus non-nociceptive pain, and acute pain versus chronic pain. Examples of other common categories of pain used by those skilled in the art include mechanical pain, neuropathic pain and phantom pain.

As used herein, the term "mechanical pain" refers to pain other than headache pain that is not neuropathic or a result of exposure to heat, cold or external chemical stimuli. Mechanical pain includes physical trauma (other than thermal or chemical burns or other irritating and/or painful exposures to noxious chemicals) such as postsurgical pain and pain from cuts, bruises and broken bones; toothache, denture pain; nerve root pain; osteoarthritis; rheumatoid arthritis; fibromyalgia; meralgia paresthetica; back pain; cancer-associated pain; angina; carpel tunnel syndrome; and pain resulting from bone fracture, labor, hemorrhoids, intestinal gas, dyspepsia, and menstruation. Itching conditions that may be treated include psoriatic pruritis, itch due to hemodialysis, aguagenic pruritus, and itching associated with vulvar vestibulitis, contact dermatitis, insect bites and skin allergies.

The term "nociception" as used herein refers to the transduction of noxious or potentially injurious stimuli into a sensation.

The term "nociceptive pain" as used herein refers to pain caused by activity in primary sensory pain fibers in the peripheral nervous system. Neurons in the peripheral nervous system that typically respond to noxious or painful stimuli are commonly referred to as nociceptors or nociceptive neurons. Yet further, the nociceoptive pathways extend to the somatosensory cortex.

The term "non-nociceptive pain" as used herein refers to pain caused by activity in neurons in the central nervous system. Examples of neurons in the central nervous system that may cause non-nociceptive pain include neurons in the dorsal horn of the spinal cord such as interneurons and projection neurons, or neurons in parts of the brain known to be involved in pain sensation such as the rostral ventromedial medulla (RVM) and the periaqueductal grey (PAG).

The term "acute pain" as used herein refers to pain that is transient in nature or lasting less than 1 month. Acute pain is typically associated with an immediate injurious process such as soft tissue damage, infection, or inflammation, and serves the purpose of notifying the subject of the injurious condition, thus allowing for treatment and prevention of further injury.

The term "chronic pain" as used herein refers to pain that lasts longer than 1 month or beyond the resolution of an acute tissue injury or is recurring or is associated with tissue injury and/or chronic diseases that are expected to continue or progress. Examples of chronic diseases that are expected to continue or progress may include cancer, arthritis, inflammatory disease, chronic wounds, cardiovascular accidents, spinal cord disorders, central nervous system disorder or recovery from surgery.

The term "neuropathy" as used herein refers to any condition that adversely affects the normal functioning of the nervous system. Neuropathies can originate anywhere in the central or peripheral nervous system, but only in some cases does this produce neuropathic pain.

The term "neuropathic pain" as used herein refers to pain that result from damage to or abnormal function of the nervous system itself. It may exist independently of any form of tissue injury outside of the nervous system. Examples of conditions that may lead to neuropathic pain include disease (e.g., HIV, Herpes, Diabetes, Cancer, autoimmune disorders), acute trauma (surgery, injury, electric shock), and chronic trauma (repetitive motion disorders, chemical toxicity such as alcohol, chemotherapy, or heavy metals).

The term "phantom pain" as used herein refers to a condition whereby the patient senses pain in a part of the body that is either no longer physically present due to amputation, or is known to be completely insensate due to total peripheral nerve destruction.

The term "hyperalgesia" as used herein refers to an increased sensitivity to nociceptive or painful stimuli. The term "allodynia" as used herein describes a condition whereby normally non-noxious stimuli are perceived as painful. Both hyperalgesia and allodynia can be divided into primary and secondary categories or conditions. Primary hyperalgesia/allodynia is an increase in sensitivity to painful and previously non-painful stimuli in a region of the body that has undergone tissue injury. Secondary hyperalgesia/allodynia is an increase in pain sensitivity globally and requires descending input into the periphery from various pain processing centers in the brain.

In accordance with the invention alternative embodiments also pertain to a sensory neuron mediated sensation which is, itching of the skin, a burning sensation, or a nociceptive (pain) sensation. As already mentioned above, the pain can be selected from inflammatory pain, inflammatory hyperalgesia, hyperalgesia, neuropathic pain, migraine, cancer pain, visceral pain, osteoarthritis pain, chronic pain and postsurgical pain. However, neuropathic pain is most preferred.

An inhibitor of α-tubulin acetylation in context of the invention may be any compound that impairs or interferes with the enzymatic transfer of an acetyl group from a donor molecule to α-tubulin. Preferred are, in context of the invention, such inhibitors that inhibit α-tubulin acetylation specifically and selectively in neuronal cells, such as peripheral sensory neurons. In one embodiment, the inhibitor of α-tubulin acetylation may inhibit α-tubulin acetylation via a direct interaction with the α-tubulin acetyltransferase, its RNA transcript or its coding genetic locus. Such inhibitors in context of the invention will be referred to as "α-tubulin acetyltransferase inhibitors or antagonists", or similar expressions. In other embodiments, the invention also includes inhibitors of α-tubulin acetylation that interact with other components of the acetylation reaction, for example with α-tubulin (the substrate) or the acetyl donor molecule. One example of such an inhibitor would be a genetic construct mediating a e.g. CRISPR/Cas9 gene editing of α-tubulin to create a K40 α-tubulin mutant that loses the ability of acting as an acceptor of an acetyl moiety.

As mentioned earlier, preferred embodiments of the invention pertain to α-tubulin acetyltransferase inhibitors or antagonists as inhibitors of α-tubulin acetylation. More preferably the α-tubulin acetyltransferase inhibitor or antagonist is an inhibitor or antagonist of mammalian/human Atat1.

The inhibitor of α-tubulin acetylation of the invention is preferably for use in medicine. Therefore, the inhibition of a neurological sensation in a subject may be a prevention or treatment of a noxious neurological sensation in the subject, and preferably is the prevention and/or treatment of pain, as defined herein above.

A prevention or treatment of pain in context of the herein disclosed invention preferably comprises the administration of the inhibitor to the subject suspected to suffer from, or suffering from pain. Pain preferably is selected from the group including acute mechanical pain, chronic mechanical pain, mechanical hyperalgesia, mechanical allodynia, inflammation, dental pain, cancer pain, visceral pain, arthritis pain, post-surgical pain, neuropathic pain, and labor pain.

In context of the present invention the term "subject" preferably refers to a mammal, preferably a human. The subject of the invention may be at danger of suffering from pain, or suffer from pain, wherein the pain is as defined herein above.

The inhibitor or antagonist of α-tubulin acetylation of the invention is in some embodiments selected from a compound having an inhibitory activity towards α-tubulin acetyltransferase and which is a polypeptide, peptide, glycoprotein, a peptidomimetic, an antibody or antibody-like molecules; a nucleic acid such as a DNA or RNA, for example an antisense DNA or RNA, a ribozyme, an RNA or DNA aptamer, siRNA and the like, including variants or derivatives thereof such as a peptide nucleic acid (PNA); a carbohydrate such as a polysaccharide or oligosaccharide and the like, including variants or derivatives thereof; a lipid such as a fatty acid and the like, including variants or derivatives thereof; or a small organic molecules including but not limited to small molecule ligands, small cell-permeable molecules, and peptidomimetic compounds.

The person of skill in the pertinent art is well aware of options of how to inhibit α-tubulin acetylation in a neuronal cell. Inhibitors of α-tubulin acetylation are for example disclosed and described in US 2014/0248635, which is incorporated by reference in its entirety.

As used herein, the term "α-tubulin acetyltransferase antagonist or inhibitor" means a substance that affects a decrease in the amount or rate of α-tubulin acetyltransferase expression or activity. Such a substance can act directly, for example, by binding to α-tubulin acetyltransferase and decreasing the amount or rate of α-tubulin acetyltransferase expression or, in particular, its enzymatic activity. A α-tubulin acetyltransferase antagonist or inhibitor can also decrease the amount or rate of α-tubulin acetyltransferase expression or activity, for example, by binding to α-tubulin acetyltransferase in such a way as to reduce or prevent interaction of α-tubulin acetyltransferase with its substrate; by binding to α-tubulin acetyltransferase and modifying it, such as by removal or addition of a moiety, or altering its three-dimensional conformation; and by binding to α-tubulin acetyltransferase and reducing its stability or conformational integrity. A α-tubulin acetyltransferase antagonist or inhibitor can also act indirectly, for example, by binding to a regulatory molecule or gene region so as to modulate regulatory protein or gene region function and affect a decrease in the amount or rate of α-tubulin acetyltransferase expression or activity. Thus, a α-tubulin acetyltransferase inhibitor or antagonist can act by any mechanisms that result in a decrease in the amount or rate of α-tubulin acetyltransferase expression or activity.

An α-tubulin acetyltransferase antagonist or inhibitor can be, for example, a naturally or non-naturally occurring macromolecule, such as a polypeptide, peptide, peptidomimetic, nucleic acid, carbohydrate or lipid. An α-tubulin acetyltransferase antagonist or inhibitor further can be an antibody, or antigen-binding fragment thereof, such as a monoclonal antibody, humanized antibody, chimeric antibody, minibody, bifunctional anti-body, single chain antibody (scFv), variable region fragment (Fv or Fd), Fab or F(ab)2. A α-tubulin acetyltransferase antagonist or inhibitor can also be polyclonal antibodies specific for α-tubulin acetyltransferase. A α-tubulin acetyltransferase antagonist or inhibitor further can be a partially or completely synthetic derivative, analog or mimetic of a naturally occurring macromolecule, or a small organic or inorganic molecule.

A α-tubulin acetyltransferase antagonist or inhibitor that is an antibody can be, for example, an antibody that binds to α-tubulin acetyltransferase and inhibits binding of a substrate to α-tubulin acetyltransferase, such as a binding to tubulin, or alters the activity of a molecule that regulates α-tubulin acetyltransferase expression or activity, such that the amount or rate of α-tubulin acetyltransferase expression or activity is decreased. An antibody useful in a method of the invention can be a naturally occurring antibody, including monoclonal or polyclonal antibodies or fragments thereof, or a non-naturally occurring antibody, including but not limited to a single chain antibody, chimeric antibody, bifunctional antibody, complementarity determining region-grafted (CDR-grafted) antibody and humanized antibody or an antigen-binding fragment thereof.

An α-tubulin acetyltransferase antagonist or inhibitor that is a nucleic acid can be, for example, an anti-sense nucleotide sequence, an RNA molecule, or an aptamer sequence. An anti-sense nucleotide sequence can bind to a nucleotide sequence within a cell and modulate the level of expression of α-tubulin acetyltransferase or modulate expression of another gene that controls the expression or activity of an α-tubulin acetyltransferase. Similarly, an RNA molecule, such as a catalytic ribozyme, can bind to and alter the expression of the α-tubulin acetyltransferase gene, or other gene that controls the expression or activity of α-tubulin acetyltransferase. An aptamer is a nucleic acid sequence that has a three dimensional structure capable of binding to a molecular target.

Certain preferred embodiments pertain to genetic constructs for gene editing that are used as inhibitors of α-tubulin acetylation in context of the herein described invention. By using gene editing it is possible to modulate the expression, stability or activity of the α-tubulin acetyltransferase. Alternatively, gene editing may be used to alter α-tubulin itself in order to reduce α-tubulin acetylation, for example by mutating lysine 40 which is a known target site for α-tubulin acetylation. Gene editing approaches are well known in the art and may be easily applied when the target gene sequences are known. Preferably such approaches may be used in gene therapy using viral vectors and which specifically target sensory neurons in accordance with the above descriptions.

An α-tubulin acetyltransferase antagonist or inhibitor that is a nucleic acid also can be a double-stranded RNA molecule for use in RNA interference methods. RNA interference (RNAi) is a process of sequence-specific gene silencing by post-transcriptional RNA degradation or silencing. The RNAi is initiated by use of double-stranded RNA (dsRNA)

that is homologous in sequence to the target gene to be silenced. A suitable double-stranded RNA (dsRNA) for RNAi contains sense and antisense strands of about 21 contiguous nucleotides corresponding to the gene to be targeted that form 19 RNA base pairs, leaving overhangs of two nucleotides at each 3' end (Elbashir et al., Nature 411:494-498 (2001); Bass, Nature 411:428-429 (2001); Zamore, Nat. Struct. Biol. 8:746-750 (2001)). dsRNAs of about 25-30 nucleotides have also been used successfully for RNAi (Karabinos et al., Proc. Natl. Acad. Sci. USA 98:7863-7868 (2001). dsRNA can be synthesized in vitro and introduced into a cell by methods known in the art.

Within certain preferred aspects, alpha tubulin acetylation modulators as provided herein may be used for the treatment of mechanical pain.

Another aspect of the present invention pertains to a pharmaceutical composition for use in the prevention or treatment of pain. The pharmaceutical composition of the invention comprises an inhibitor of α-tubulin acetylation as described herein above, and a pharmaceutical acceptable carrier and/or excipient.

As used herein the language "pharmaceutically acceptable carrier" is intended to include any and all solvents, solubilizers, fillers, stabilizers, binders, absorbents, bases, buffering agents, lubricants, controlled release vehicles, diluents, emulsifying agents, humectants, lubricants, dispersion media, coatings, antibacterial or antifungal agents, isotonic and absorption delaying agents, and the like, compatible with pharmaceutical administration. The use of such media and agents for pharmaceutically active substances is well-known in the art. Except insofar as any conventional media or agent is incompatible with the active compound, use thereof in the compositions is contemplated. Supplementary agents can also be incorporated into the compositions. In certain embodiments, the pharmaceutically acceptable carrier comprises serum albumin.

The pharmaceutical composition of the invention is formulated to be compatible with its in-tended route of administration. Examples of routes of administration include parenteral, e.g., intrathecal, intra-arterial, intravenous, intradermal, subcutaneous, oral, transdermal (topical) and transmucosal administration.

Solutions or suspensions used for parenteral, intradermal, or subcutaneous application can include the following components: a sterile diluent such as water for injection, saline solution, fixed oils, polyethylene glycols, glycerine; propylene glycol or other synthetic solvents; anti-bacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the injectable composition should be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the requited particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a neu-regulin) in the required amount in an appropriate solvent with one or a combination of ingre-dients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Stertes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the pharmaceutical compositions are formulated into ointments, salves, gels, or creams as generally known in the art.

In certain embodiments, the pharmaceutical composition is formulated for sustained or controlled release of the active ingredient. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially (including liposomes targeted to infected cells with monoclonal antibodies to viral antigens) can also be used as pharmaceutically acceptable carriers. These can be prepared according to methods known to those skilled in the art.

It is especially advantageous to formulate oral or parenteral compositions in dosage unit form for ease of administration and uniformity of dosage. Dosage unit form as used herein includes physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharma-ceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of ad-ministration utilized. For any compound used in the method of the invention, the therapeuti-cally effective dose can be estimated initially from cell culture assays. A dose may be formu-lated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. The pharmaceutical compositions can be included in a container, pack, or dispenser together with instructions for administration.

Yet another aspect of the invention pertains to a method for inhibiting a neurological sensation mediated by sensory neurons in a subject, the method comprising a step of inhibiting or reducing in a sensory neuron of the subject the acetylation of α-tubulin. Preferably the method comprises a step of introducing into the sensory neuron an inhibitor of α-tubulin acetylation, preferably an inhibitor of α-tubulin acetyltransferase (Atat1).

In some embodiments the method of the invention may further comprise a step of administering to the subject an inhibitor of α-tubulin acetyltransferase.

Other embodiments of the method are provided which are for treating a subject suffering from a pathology associated with a neurological sensation, preferably wherein the pathology is pain such as acute mechanical pain, chronic mechanical pain, mechanical hyperalgesia, mechanical allodynia, inflammation, dental pain, cancer pain, visceral pain, arthritis pain, post-surgical pain, neuropathic pain, and labor pain.

Antagonists of the herein described invention are preferably selected from the group of compounds consisting of inhibitory RNA, inhibitory antibodies or fragments thereof, and/or small molecules. A detailed description of inhibitors and antagonists of acetylation of α-tubulin is provided herein above.

In context of the invention it is also preferred that at least one additional therapeutic compound effective against pain, for example a morphine, an opioid or a non-opioid analgesic or other analgesic, is administered to said subject.

The diseases treatable in context of the afore-described methods are described herein above.

During the treatment or prevention it is preferred that at least one additional therapeutic effective against pain is administered to said patient, such as other analgesics, for example an opioid or a non-opioid analgesic.

The above problem in the prior art is furthermore solved by a screening method for identifying a compound useful for inhibiting a mechanically induced, or chronical, neurological sensation comprising the steps of:

(a) Contacting (i) a biological cell expressing an α-tubulin acetyltransferase gene, and/or (ii) a α-tubulin acetyltransferase protein, with a candidate compound;

(b) Determining at least one of α-tubulin acetyltransferase enzymatic activity or expression; and (c) Comparing the activity, and/or the expression, as determined in step (b) with the activity or expression of the α-tubulin acetyltransferase in the absence of the candidate compound, wherein a decrease between the measured activities and/or expression of the α-tubulin acetyl-transferase indicates that the candidate compound is an inhibitor of the α-tubulin acetyltransferase and that the candidate compound is useful for inhibiting a mechanically induced neurological sensation.

Some embodiments relate to the above method which is an ex vivo or in vitro method.

The compound identified by the screening methodology of the invention is preferably then suitable for use in the treatment of pain.

Candidate compounds for the screening are preferably selected from a polypeptide, peptide, glycoprotein, a peptidomimetic, an antibody or antibody-like molecule; a nucleic acid such as a DNA or RNA, for example an antisense DNA or RNA, a ribozyme, an RNA or DNA aptamer, siRNA and the like, including variants or derivatives thereof such as a peptide nucleic acid (PNA); a carbohydrate such as a polysaccharide or oligosaccharide and the like, including variants or derivatives thereof; a lipid such as a fatty acid and the like, including variants or derivatives thereof; or a small organic molecules including but not limited to small molecule ligands, small cell-permeable molecules, and peptidomimetic compounds.

Some embodiments of the screening method make use of assays, wherein expression of the α-tubulin acetyltransferase is determined by detecting α-tubulin acetyltransferase mRNA, for example using a PCR based assay, or by detecting α-tubulin acetyltransferase protein, for example immunologically. Assays for detecting or quantifying mRNA expression are well known to those skilled in the art. Such assays could be qualitative or quantitative, however, the latter is preferred.

In alternative or additional embodiments the α-tubulin acetyltransferase activity may be determined by measuring the α-tubulin acetylation. In this aspect the above screening method may be adapted from a screening of biological cells, to a cell free assay system suitable to measure α-tubulin acetylation. In this embodiment the above screening method is altered such that instead of a "biological cell" a "cell-free system" is provided. A cell free system for assessing α-tubulin acetylation may include as components isolated or recombinantly expressed α-tubulin, an acetylation donor such as acetyl-CoA, and an isolated or recombinantly expressed α-tubulin acetyltransferase. The amount of α-tubulin acetylation in the system in presence or absence of the candidate compound is then determined by monitoring the reaction by either monitoring the decline of the donor molecule or the conversion of α-tubulin to acetylated α-tubulin.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The present invention will now be further described in the following examples with reference to the accompanying figures and sequences, nevertheless, without being limited thereto. For the purposes of the present invention, all references as cited herein are incorporated by reference in their entireties. In the Figures.

EXAMPLES

Figure 1A:
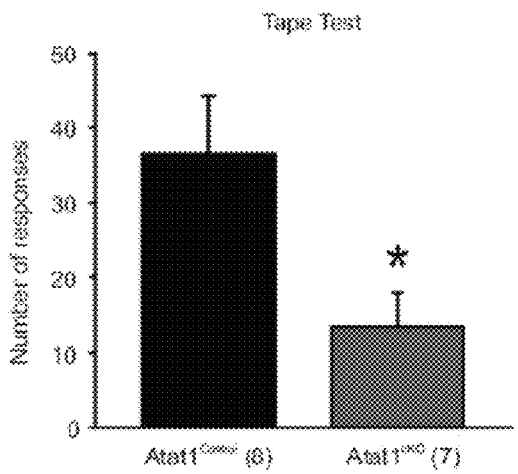
FIG. 1A is a bar chart summarising the results of a tape test to assay low threshold mechanosensation. Atat1$^{cKO}$ mice demonstrated significantly less response events over the 5 minute counting period (t-Test, P<0.05).

Materials and Methods
Animals and Behavioural Experiments

To study the effect on touch sensitivity of deleting the ATAT1 gene we crossed ATAT1$^{fl/+}$ mice[17] with a peripheral nervous system specific Cre line Avil$^{cre/+}$ mouse line[18] to obtain Avil-Cre::ATAT1$^{fl/+}$ (control) and Avil-Cre::Atat1$^{fl/+}$ (cKO) animals. Mice were genotyped as described previously[18,19] and maintained at the EMBL Mouse Biology Unit, Monterotondo, Italy, in accordance with Italian legislation (Art. 9, 27 Jan. 1992, no 116) under license from the Italian Ministry of Health.

For the tape response assay mice were left to acclimate in plexiglass containers for 15 min. A 3 cm long by 1 cm wide piece of tape (Identi tape) was then gently applied along the spinal column on the back of the animal. The mice were then monitored for 5 min and the number of behavioural responses recorded. A response was recorded whenever a mouse attempted to remove the tape by scratching, biting or shaking.

For the cotton swab test, mice were placed in plexiglass boxes atop an elevated mesh base, and allowed to habituate for 30 min. A cotton swab was then 'puffed out' by pulling with forceps to increase its size. This enlarged swab was then applied to the hind paw of the animal using a gentle brushing manner, firstly to the right and subsequently the left hind paw.

For von Frey testing, mice were placed inside an open topped plexiglass container on an elevated mesh platform to acclimate for 1 h. A series of von Frey filaments (North Coast Medical, NC12775-99) with final force of 0.02 g to 1 g were applied to the animal's hind paw alternating left and right paw and a yes/no paw withdrawal response was recorded.

For the Tail clip assay, an alligator clip, covered with rubber tubing (to reduce tissue damage) and calibrated to exert 400 g force was attached to the base of the tail of Atat1$^{Control}$ and Atat1$^{cKO}$ mice Animals were placed in plexiglass containers and the latency to awareness of the clip as indicated by biting, vocalization or grasping was measured.

For the hot plate assay mice were placed on a hot plate (Ugo Basile, 35150) pre-heated to 55° C. and latency time was measured until a jump, hind paw flick or hind paw lick were observed. In case of the lack of any response the mice were removed from the hot plate after 30 s.

A modified version of the rotarod test was performed on naive Atat1$^{Control}$ and Atat1$^{cKO}$ mice. Briefly, mice were habituated for 5 mM to the stationary dowels of the rotarod (Rotarod 3375-5 TSE systems). Each step, either habituation or test was followed by a 5 minute rest period with food and water ad libitum. Mice were then habituated for 5 mM to the moving dowels at 5 RPM. Following this the mice were tested at 5, 10, 15, 20 and 25 RPM respectively for 2 mM a trial. The time spent on the dowels was then calculated. A fall or two full spins while gripping the dowel was considered a fail during the test.

Ex Vivo Electrophysiology

The skin nerve preparation was used essentially as previously described[27]. Briefly, mice were sacrificed using CO2 inhalation, and the saphenous nerve together with the skin of the hind limb was dissected free and placed in an organ bath. The chamber was perfused with a synthetic interstitial fluid (SIF buffer) consisting of (in mM): NaCl, 123; KCl, 3.5; MgSO4, 0.7; NaH2PO4, 1.7; CaCl2, 2.0; sodium gluconate, 9.5; glucose, 5.5; sucrose, 7.5; and HEPES, 10 at a pH of 7.4.) The skin was placed with the corium side up, and the nerve was placed in an adjacent chamber for fiber teasing and single-unit recording. Single units were isolated with a mechanical search stimulus applied with a glass rod and classified by conduction velocity, von Frey hair thresholds and adaptation properties to suprathreshold stimuli. A computer-controlled nanomotor (Kleindiek Nanotechnik) was used to apply mechanical ramp-and-hold stimuli of known amplitude and velocity. Standardized displacement stimuli of 2 s or 10 s duration were applied to the receptive field at regular intervals (interstimulus period, 30 s). The probe was a stainless steel metal rod with a flat circular contact area of 0.8 mm. The signal driving the movement of the linear motor and raw electrophysiological data were collected with a Powerlab 4.0 system and Labchart 7.1 software (AD instruments), Spikes were discriminated off-line with the spike histogram extension of the software.

Patch Clamping

DRG neurons were collected from mice and dissociated as described[27]. In some cases they were transfected using the Nucleofector system (Lonza AG) in 20 μl of Mouse Neuron Nucleofector solution from the SCN nucleofector kit (Lonza AG) and a total 4-5 μg of plasmid DNA at room temperature using the preinstalled program SCN Basic Neuro program 6. After electroporation, the cell suspension was transferred to 500 μl of RPMI 1640 medium (Gibco) for 10 min at 37° C. This suspension, supplemented with 10% horse serum, was used to plate the cells onto glass coverslips for recording. The RPMI medium supplemented with 100 ng/ml nerve growth factor (NGF), 50 ng/ml BDNF was replaced with the standard DRG medium 3-4 h later. Electrophysiology experiments began 12 h after plating.

Whole-cell recordings from isolated DRG neurons were made as previously described[23]. Recordings were made from DRG neurons using fire-polished glass electrodes with a resistance of 3-7 Mg. Extracellular solution contained (mM): NaCl 140, MgCl2 1, CaCl2 2, KCl 4, glucose 4 and HEPES 10 (pH 7.4), and electrodes were filled with a solution containing (mM): KCl 130, NaCl 10, MgCl2 1, EGTA 1 and HEPES 10 (pH 7.3). Cells were perfused with drug-containing solutions by moving an array of outlets in front of the patched cells (WAS02; Ditel, Prague). Observations were made with Observer A1 inverted microscope (Zeiss) equipped with a CCD camera and the imaging software AxioVision. Membrane current and voltage were amplified and acquired using EPC-10 amplifier sampled at 40 kHz; acquired traces were analyzed using Patchmaster and Fitmaster software (HEKA). Pipette and membrane capacitance were compensated using the auto function of Pulse. For most of the experiments, to minimize the voltage error, 70% of the series resistance was compensated and the membrane voltage was held at −60 mV with the voltage-clamp circuit. After establishing whole-cell configuration, voltage-gated currents were measured using a standard series of voltage commands Briefly, the neurons were pre-pulsed to −120 mV for 150 ms and depolarized from −65 to +55 mV in increments of 5 mV (40 ms test pulse duration). Next the amplifier was switched to current-clamp mode and current injection was used to evoke action potentials. If the membrane capacitance and resistance changed more than 20% after the mechanical stimulus, the cell was regarded as membrane damaged and the data discarded. Mechanical stimuli were applied using a heat-polished glass pipette (tip diameter 3-5 μm), driven by a MM3A Micromanipulator system (Kleindiek), and positioned at an angle of 45 degrees to the surface of the dish. The probe was positioned near the neurite, moved forward in steps of 200-600 nm for 500 ms and then withdrawn. For analysis of the kinetic properties of mechanically activated current, traces were fit with single exponential functions using the Fitmaster software (HEKA). Data are presented as mean±s.e.m.

Immunofluorescence and Staining

For microtubule staining in DRG cultures, cells were washed once with PBS, and then fixed for 15 mM in cytoskeleton buffer (CB) pH 6.3 containing 3% paraformaldehyde, 0.25% triton and 0.2% glutaraldehyde at room temperature. Cells were then washed 3 times with PBST (0.3% triton). Samples were then subsequently blocked with 5% normal goat serum (NGS) in PBS for 1 h at room temperature. Cells were then placed overnight at 4° C. with primary anti α-tubulin (1:1000) (Sigma-Aldrich, T9026) or anti-acetylated-α-tubulin (1:1000) (Sigma-Aldrich, T7451) in PBS. Cells were then washed with PBS and incubated for 1 h with fluorescently labelled secondary antibodies (1:1000) (Alexa Fluor 546 Lifetechnologies) for 1 h at room temperature. All images were acquired using a 40× objective on a Leica SP5 confocal microscope. Processing of images and generation of surface plots were performed using ImageJ Images were deconvoluted using Huygens software.

Actin filaments in DRG primary cultures were stained with Alexa488-phalloidin at 0.5 μg/ml (Lifetechnologies). Briefly cells were fixed with fresh 4% PFA (EM grade, TAAB) in cytoskeleton buffer (10 mM MES, 138 mM KCl, 3 mM MgCl, 2 mM EGTA) freshly added supplemented of 0.3 M sucrose, permeabilized in 0.25% Triton-X-100 (Sigma-Aldrich), and blocked in 2% BSA (Sigma-Aldrich).

Immunostaining of saphenous nerves was performed on paraffin sections after fixation with PFA. Following rehydration, antigen retrieval was performed with 10 mM sodium citrate (pH 6) at boiling temperature for 10 mM. Subsequently, sections were permeabilized (0.3% Triton X-100), blocked (5% goat serum) and stained with anti-acetylated-α-tubulin (Sigma-Aldrich, T7451) and anti-myelin basic protein (Chemicon, MAB386).

For cornea staining, the eyes were removed and fixed for 1 h in 4% PFA at room temperature. The cornea was then dissected and permeabilized with PBS-Triton 0.03% for 30 mM. Following this, the cornea was immersed in PBS-Triton 0.03% containing 1 μM SNAP surface 546 (New England Biolabs) for 30 min. The samples were then washed with PBS-Triton 0.03% for 20 min and subsequently blocked with 5% normal goat serum in PBS-Triton 0.03% for 30 mM. The tissue was then stained with anti-acetylated-α-tubulin (1:500) overnight. Samples were then washed with PBS and a secondary antibody (Alexa Fluor 488 Life-technologies) was added for 5 h. The samples were again washed with PBS and stained with DAPI 10 mM. The cornea was then mounted on glass with 100% glycerol and imaged.

For whole mount axon outgrowth assays, individual DRG were extracted from mice and grown in Matrigel (Corning) for 7 days. Preparations were fixed with 4% PFA for 5 minutes and labelled with the primary antibody PGP9.5 (1:200) overnight at 4° C. The samples were then labeled with secondary antibodies (1:1000) Alexa Fluor 546 Lifetechnologies) for 1 h at room temperature. All images were acquired using a Leica LMD 7000.

SNAP-tag labelling was carried out by intradermal injection of the finger in anaesthetized mice of 2 ∞M BG TMRstar substrate as described previously[28]. After five hours the animals were sacrificed and the samples were mounted in 80% glycerol for imaging.

Electron Microscopy of Saphenous Nerve

Saphenous nerves were dissected and postfixed for 24 h with fresh 4% (w/v) PFA, 2.5% (w/v) Glutaraldehyde (TAAB) in 0.1 M Phosphate buffer at 4 C. Following postfixation, the samples were incubated for 2 h with 1% (w/v) OsO4 supplemented with 1.5% (w/v) Potassium Ferrocyanide, samples were dehydrated in Ethanol and infiltrated with propylene oxide/Epon (Agar) (1:1) followed by resin embedding. Ultrathin sections were cut (Ultracut S, Leica), counter-stained with Uranyl Acetate and Lead Citrate and observed with a Transmission Electron Microscope (TEM) Jeol 1010 equipped with a MSC 791 CCD camera (Gatan).

Microfluidics

DRG neurons were suspended in 1:1 Matrigel in 10% FBS DMEM and seeded onto a two-chamber microfluidic chip (Xona Microfluidics, SD150). Axons were allowed to grow across the microchannels connecting the two chambers for 3-5 days. On the day of the experiment, media in both the cell body and axon chambers was replaced with media with no serum for 3 h. 1 μM mono-biotinylated NGF purified in house from eukaryotic cells was coupled with 1 μM streptavidin conjugated quantum dots 655 (Life Technologies) for 30 min on ice, then diluted to 5 nM in imaging buffer (as above) and then used to replace the media in the axon chamber. A 25% volume difference was kept between the cell body and the axon chamber to avoid backflow from the axon to the cell body chamber. After 1 h incubation at 37° C. in 5% CO2, retrograde transport of NGF-Qdot655 containing endosomes was imaged using a confocal Ultraview Vox (Perkin Elmer) equipped with a 5% CO2 humidified chamber at 37° C. 100 s time lapses were recorded using 300 ms exposure time Images were analyzed with Imaris software using the particle tracking function and autoregressive motion track generation setting.

Superresolution Microscopy

The cells were washed once with 3 ml of warm PBS. Subsequently, the cells were fixed and permeabilized for 2 min in cytoskeleton buffer containing 0.3% Glutaraldehyde and 0.25% Triton X-100. Following this, the cells were fixed for 10 min in cytoskeleton buffer containing 2% Glutaraldehyde and treated for 7 min with 2 ml of 0.1% Sodium Borohydride (NaBH4) in PBS. Cells were then washed 3 times for 10 min in PBS. The cells were incubated with primary antibody for 30 min (mouse anti α-tubulin, Neomarker, 1:500) in PBS+2% BSA After washing 3 times for 10 min with PBS, the cells were transferred to the secondary antibody (goat anti mouse Alexa 647, 1:500, Molecular Probes A21236) at room temperature for 30 min. The cells were then washed 3 times with PBS for 10 min and then mounted for PALM imaging. At the time of imaging cells were overlaid with PALM blinking buffer: 50 mM Tris pH 8.0, 10 mM NaCl, 10% Glucose, 100 U/ml Glucose Oxidase (Sigma-Aldrich), 40 ug/ml Catalase (Sigma-Aldrich).

The analysis of microtubule (MT) network morphology was done using the open source software CellProfiler[29]. The MT signal was enhanced by a top-hat filter and then binarised with the same manual threshold for all images. Binary images were skeletonized using CellProfiler's "skelPE" algorithm and the resulting skeleton was subjected to branchpoint detection. As an approximation for MT network complexity we divided the number of branchpoints by the number of pixels in the skeleton. Moreover, we measured the local angular distribution of the MTs in order to assess whether they run in parallel, or in a crossing manner (angular variance). To this end, we subjected each pixel to a rotating morphological filter using a linear structural element with a length of 11 pixels, and recorded at which angle we obtained a maximum response. The inventors computed the response for angles from 0 to 170 degrees at steps of 10 degrees since there is no information on MT polarity. Next we measured the local circular variance[3] of the MT orientations in a sliding window with a diameter of 51 pixels, using angle doubling as it is commonly done for axial data[3]. The circular variance has a value 1 if the MTs in a given region are completely parallel and has smaller values (down to 0) if the MTs are oriented in various directions. Finally, we computed the average circular variance of all MT pixels in a given cell. If this value were close to 1 it would mean that locally, on a length scale of 51 pixels, the MTs are parallel in most of the cell.

Atomic Force Microscopy (AFM)

Force spectroscopy measurements were performed by using a NanoWizard AFM (JPK Instruments, Berlin, Germany) equipped with a fluid chamber (Biocell; JPK) for live cell analysis and an inverted optical microscope (Axiovert 200; Zeiss) for sample observation.

DRG cells were seeded on glass coverslip previously coated with a first layer of polylysine (500 µg/ml for about 1 h room temperature) and a second layer of laminin (20 µg/ml for about 1 h at 37° C.). The cells were then cultured for at least 15 h before measurements. Then, the sample was inserted into the fluid chamber (Biocell; JPK) immersed in culture medium and measurements were carried out at room temperature. The status of cells was constantly monitored by optical microscope.

Indenters for probing cell elasticity were prepared by mounting silica microspheres of 4.5 µm nominal diameter (Bangs Laboratories Inc.) to tipless V-shaped silicon nitride cantilevers having nominal spring constants of 0.32 N/m or 0.08 N/m (NanoWorld, Innovative Technologies) by using UV sensitive glue (Loxeal UV Glue). Silica beads were picked under microscopy control. Before measurements the spring constant of the cantilevers was calibrated by using the thermal noise method.

By using the optical microscope the bead-mounted cantilever was brought over the soma of single DRG and pressed down to indent the cell. The motion of the z-piezo and the force were recorded. On each cell eight-about ten force-distance curves were acquired with a force load of 500 pN and at a rate of 5 µm sec-1 in closed loop feed-back mode.

Cell elastic properties were assessed by evaluating the Young's modulus (E) of the cell. This value was obtained by analyzing the approaching part of the recorded F-D curves using the JPK DP software. The software converts the approaching curve into force-indentation curves by subtracting the cantilever bending from the signal height to calculate indentation. Afterwards force-indentation curves were fitted by Hertz-Sneddon model for a spherical indenter according to this equation:

$$F = \frac{E}{1-v^2}\left[\frac{a^2 + R_s^2}{2}\ln\frac{R_s + a}{R_s - a} - aR_s\right]$$

$$\delta = \frac{a}{2}\ln\frac{R_s + a}{R_s - a}$$

Here, $\delta$ is the indentation depth, a is the contact radius of the indenter, R is the silica bead radius, v is the sample's Poisson ratio (set to 0.5 for cell)[30] and E is Young's modulus. Fitting was performed at different indentations 200, 400 and 600 nm (see SI for examples of fitting curves obtained).

For Young's modulus values, the statistical difference between two groups of data was evaluated by using the non-parametric statistical analysis of the Mann-Whitney test (two-tailed distribution) by GraphPad Prism 5.0. A p value <0.05 was considered statistically significant.

Osmotic Shrinking Assays

Cultured DRG were loaded with 500 nM C8 SIR-Tubulin for 1 h at 37° C. and/or 2 µM calcein dye (Invitrogen C3100MP) for 30 mM in DRG at 37° C. The cells were then transferred to imaging buffer (10 mM Hepes pH 7.4, 140 mM NaCl, 4 mM KCl, 2 mM CaCl2, 1 mM MgCl2, 5 mM D-glucose) at 320 mOsm. Following a 5 mM acclimatization period the cells were subjected to a 440 mOsm (osmolarity adjusted with mannitol) hyperosmotic shock for 3 min. All imaging was carried out using a Leica SP5 resonant scanner.

Example 1

Conditional Atat1 Knock-Out Mice Have Impaired Sensation of Mechanical Innoxious and Noxious Stimuli To investigate cell autonomous effects of Atat1 disruption in sensory neurons the inventors took a conditional gene deletion strategy. Atat1$^{fl}$ mice[18] were crossed with a sensory neuron specific Cre driver line Avil-Cre[19] to generate Avil-Cre::Atat1$^{fl/fl}$ (referred to as Atat1$^{cKO}$) and control Avil-Cre::Atat1$^{fl/+}$ mice (referred to as Atat1$^{Control}$). Mice were then subjected to a series of behavioural assays. The inventors first tested their ability to detect an innocuous mechanical stimulus applied to the hairy skin. Adhesive tape was fixed gently to the backs of animals and the number of responses counted over a 5 minute observation period. While control mice made regular attempts to remove the tape, Atat1$^{cKO}$ mice effectively ignored it for much of the time, and the total number of responses was significantly lower (FIG. 1a).

Figure 1B:
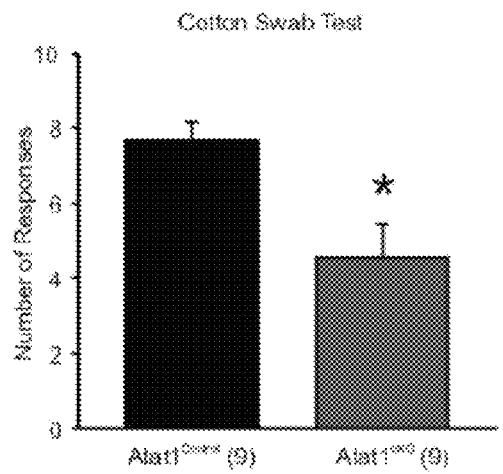
FIG. 1B is a bar chart showing the cotton swab analysis assaying low threshold mechanosensation. Atat1$^{cKO}$ mice demonstrated significantly less response events then Atat1$^{Control}$ counterparts (t-Test, P<0.01).
Figure 1C:
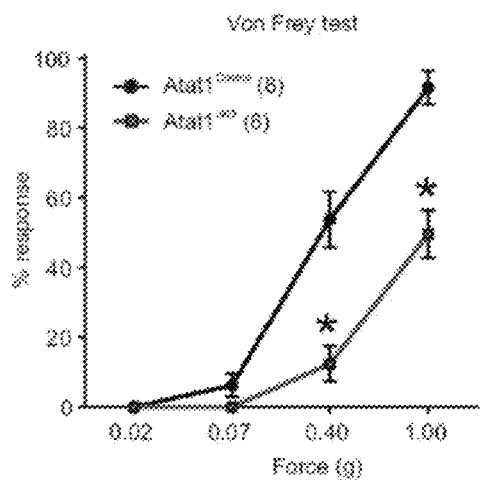
FIG. 1C is a graph of von Frey thresholds showing the significantly lower response frequency in Atat1$^{cKO}$ animals (RM ANOVA, Holm-Sidak method, P<0.001).

The inventors next investigated the sensitivity of mice to innocuous mechanical stimuli applied to the glabrous skin by lightly stroking the underside of the paw with a diffuse cotton swab[20]. Again, Atat1$^{cKO}$ mice responded significantly less to this stimulus than Atat1$^{Control}$ mice (FIG. 1b). The inventors also examined whether mechanical sensitivity to punctate stimuli was altered in Atat1$^{cKO}$ mice by applying von Frey filaments of calibrated forces to the hindpaw of mice. Control animals responded to forces as low as 0.07 g with a linear increase in detection into the noxious range. However, Atat1$^{cKO}$ mice required significantly higher forces to evoke a response throughout the range of von-Frey filaments (FIG. 1c).

Figure 1D:
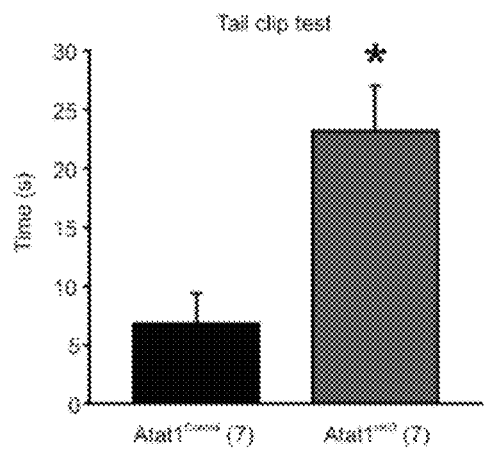
FIG. 1D is a bar chart showing latency to awareness of a clip attached to the base of the tail. Atat1$^{cKO}$ animals take significantly longer to respond to the stimulus (t-Test, P<0.01).

To investigate noxious mechanical sensitivity in more detail, the inventors analysed responses to a clip applied to the base of the tail. Atat1$^{cKO}$ mice displayed substantially longer latencies to awareness of the clip compared to Atat1$^{Control}$ mice and again, essentially ignored it for much of the time (FIG. 1d).

Figure 1E:
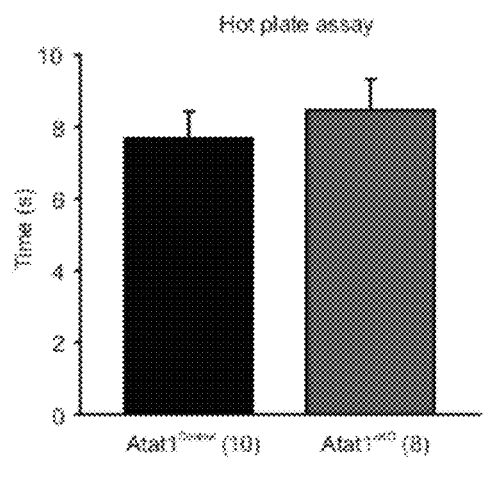
FIG. 1E is a bar chart showing that there are no significant differences in the responses recorded to noxious heat between Atat1$^{cKO}$ and Atat1$^{Control}$ animals (t-Test, P>0.05).
Figure 1F:
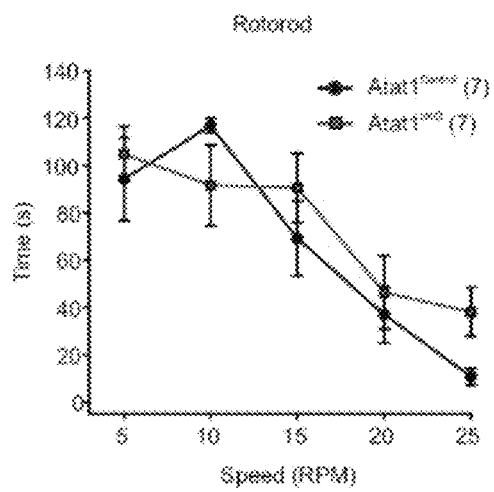
FIG. 1F is a bar chart showing that there are no significant differences in motor performance as assayed using the Rotorod test (RM ANOVA, Holm-Sidak method, P>0.05). Error bars indicate s.e.m.

The inventors further tested whether noxious thermal detection was effected by Atat1 deletion by measuring the time to response on a hotplate. The inventors observed no difference in withdrawal latencies to noxious temperatures between Atat1$^{cKO}$ and Atat1$^{Control}$ mice (FIG. 1e). Finally the inventors assessed the motor coordination of Atat1$^{cKO}$ mice by evaluating their performance on a rotorod device. Atat1$^{cKO}$ and Atat1$^{Control}$ mice displayed statistically similar latencies to fall from the rotating drum across all speeds tested. Thus, Atat1 is required for the detection of innocuous and noxious mechanical touch but not for noxious heat or proprioceptive coordination.

Example 2

Figure 2A:
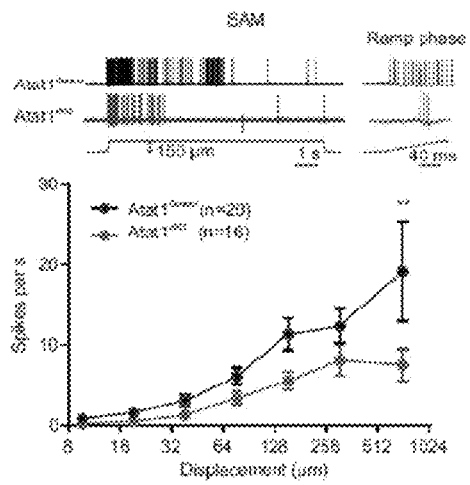
FIG. 2A shows responses (top) and stimulus-response function (bottom) of slowly adapting mechanoreceptor fibers (SAM)
Figure 2B:
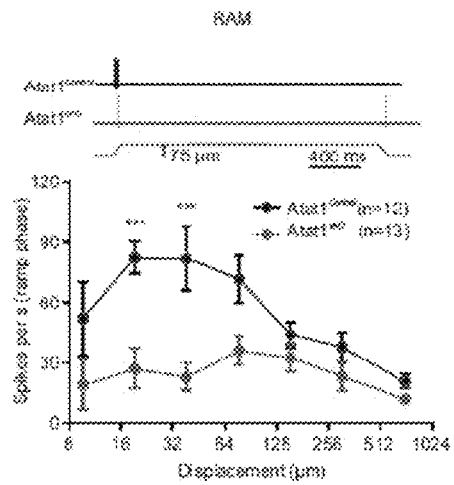
FIG. 2B shows rapidly adapting mechanoreceptor fibers (RAM)
Figure 2C:
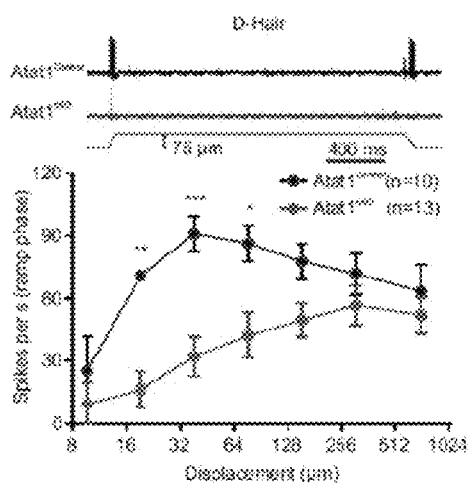
FIG. 2C shows D-hair afferents.
Figure 2D:
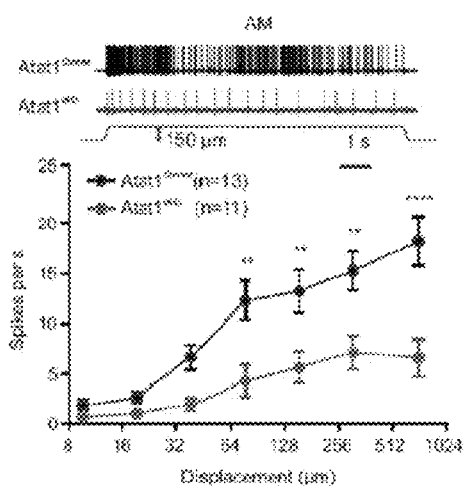
FIG. 2D shows Aδ-mechanonociceptors (AM) and FIG. 2E show C-fibre nociceptors from αTAT1control and αTAT1cko mice (two-way ANOVA with post-hoc Bonferroni's test, SAM: P<0.001; RAM: P<0.0001; D-hair: P<0.0001; AM: P<0.0001; C-fibre: P<0.0001).
Figure 2E:
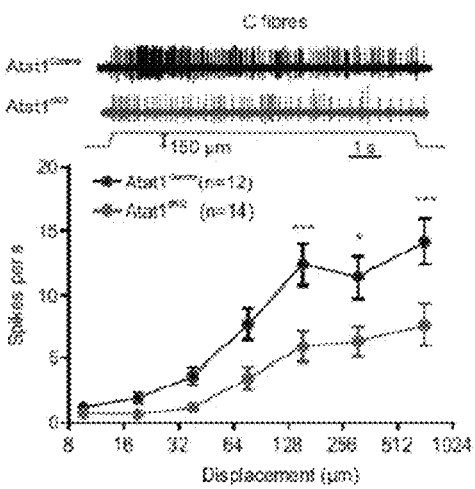
Figure 2F:
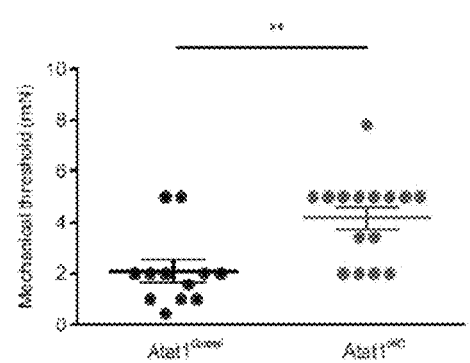
FIG. 2F shows Mean von Frey thresholds for C fibre discharge (Mann-Whitney test, P<0.01). The number of fibres recorded is indicated in parentheses in each panel. *P<0.05; P<0.01; *P<0.001; ****P<0.0001. Error bars indicate s.e.m.

Sensory Neuron Electrophysiological Responses are Impaired in Atat1 Conditional Knockout Mice Sensory neuron axons terminate in the skin and form a diverse range of functionally distinct mechanoreceptors that underlie the sense of touch[1]. They can be classified by their conduction velocity (into Aβ, Aδ and C fibres), their adaptation properties (into rapidly adapting or slowly adapting) and by their mechanical thresholds. To determine how Atat1 deletion affects each of these populations and regulates touch sensitivity, the inventors utilized an ex vivo skin-nerve preparation to record from single cutaneous sensory neurons in the saphenous nerve. The inventors first considered fast conducting Aβ fibres, separating them into slowly adapting (SAM) and rapidly adapting (RAM) mechanoreceptors. The inventors observed a striking reduction in the mechanical sensitivity of SAM fibres that was apparent as a reduced number of action potentials per stimulus indentation (FIG. 2a) and a ~10-fold increase in the latency of the response in Atat1$^{cKO}$ mice. Reductions in firing frequencies were evident during both the ramp phase of the mechanical stimulus and during the static phase. RAM fibres displayed a similar reduction in their stimulus response function (FIG. 2b) and an increased latency to the highest displacement stimulus. A characteristic of these fibres is that they display higher firing frequencies with increasing stimulus speed[21], a feature which was also reduced in Atat1$^{cKO}$ mice. Mechanical, electrical thresholds and conduction velocities were unchanged in Aβ fibres in the absence of Atat1. The inventors next examined Aδ fibres which can be classified as D-hair and Aδ-mechanonociceptors (AM) units by their mechanical threshold and adaptation properties. Both populations of mechanoreceptor displayed significant reductions in their stimulus response function (FIGS. 2c and d), longer latencies for mechanical activation, and decreased sensitivity to dynamic stimuli. Electrical thresholds and conduction velocities were unchanged in the absence of Atat1. Finally the inventors considered C-fibres, the largest population of sensory afferents. Similar to all other fibre types, C-fibres exhibited a reduced number of action potentials evoked by indentation stimuli (FIG. 2e), and no change in electrical properties or conduction velocity. Strikingly, mechanical thresholds of C-fibres were also significantly elevated in Atat1$^{cKO}$ mice (FIG. 2f). Thus Atat1 is required for mechanical sensitivity across all major fibre types innervating the skin.

Example 3

Modulation of Atat1 Enzymatic Activity Regulates Mechanosensitivity

Figure 3A:
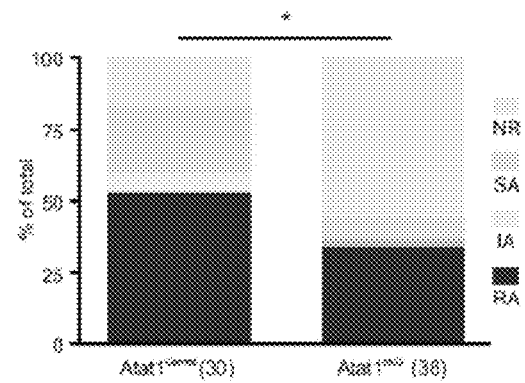
FIG. 3A shows stacked histograms showing the proportion of different mechanogated currents activated by neurite indentation in sensory neurons from control Atat1$^{Control}$ and Atat1$^{cKO}$ mice ($\chi^2$ test, P<0.05). NR, non-responsive to given displacement 512 nm.
Figure 3B:
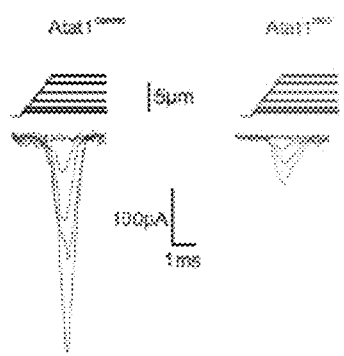
FIG. 3B shows representative traces of RA currents elicited by increasing probe displacement on soma of Atat1$^{Control}$ and Atat1$^{cKO}$ sensory neurons.
Figure 3C:
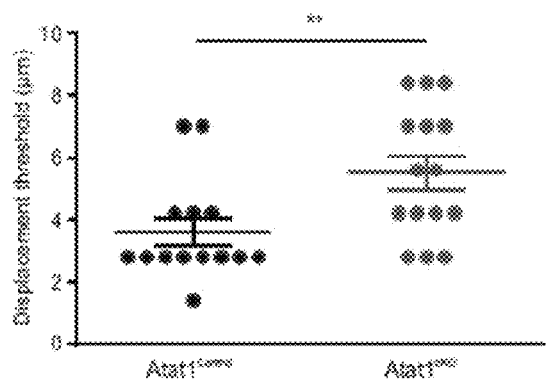
FIG. 3C shows threshold of activation of RA currents was determined as mechanical stimulus that elicited a current ≥20 pA. Closed circles indicate individual recorded cells. Note the marked increase in the displacement threshold in Atat1$^{cKO}$ sensory neurons (Mann-Whitney test, P<0.01). e
Figure 3D:
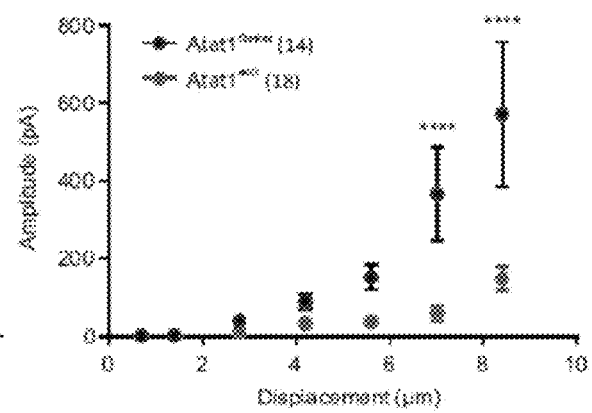
FIG. 3D shows stimulus response curve of RA currents evoked by increasing probe displacement. Genetic depletion of αTAT1 in sensory neuron significantly reduced RA-currents amplitude (two-way ANOVA with post-hoc Bonferroni's test, P<0.0001).

To determine how deletion of Atat1 influences mechanotransduction in sensory neurons the inventors recorded mechanosensitive currents from cultured DRG neurons indented with a blunt glass probe. Such a stimulus can evoke mechanically gated currents in ~90% of DRG neurons that are further classified as rapidly adapting (RA), intermediate-adapting (IA) and slowly adapting (SA) responses[23]. In the absence of Atat1, the inventors observed a marked loss in the number of mechanically sensitive neurons in the DRG that was evident across each subtype of current (FIG. 3a). Furthermore, the small proportion of neurons which still displayed mechanosensitive currents in Atat1$^{cKO}$ mice exhibited significantly reduced current amplitudes and higher thresholds (FIG. 3b-d), but no difference in their activation kinetics. Other functional parameters such as voltage gated channel activity, resting membrane potential, action potential threshold, and pH sensitivity were indistinguishable between Atat1$^{Control}$ and Atat1$^{cKO}$ mice indicating that the reduced mechanical sensitivity of DRG neurons does not arise from compromised membrane properties.

Figure 3E:
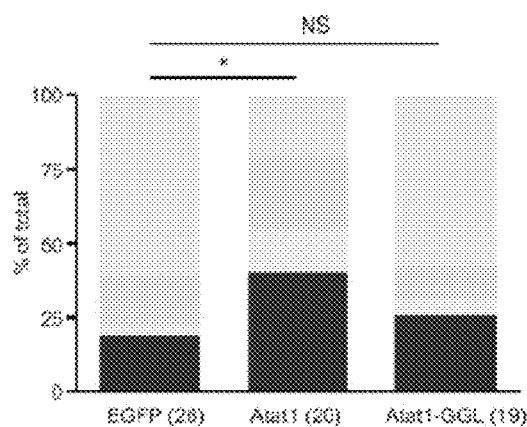
FIG. 3E shows stacked histograms showing the proportions of different mechano-gated currents observed in Atat1$^{cKO}$ sensory neurons transfected with EGFP, αTAT1-YFP or αTAT1-GGL-YFP cDNA. Transfection of wild-type αTAT1 rescued the loss of mechanosensitivity, while transfection of catalytically inactive αTAT1 (αTAT1-GGL-YFP) failed to restore it in Atat1$^{cKO}$ sensory neurons ($\chi^2$ test, EGFP versus αTAT1-YFP, P<0.05; EGFP versus αTAT1-GGL-YFP, P>0.05).
Figure 3F:
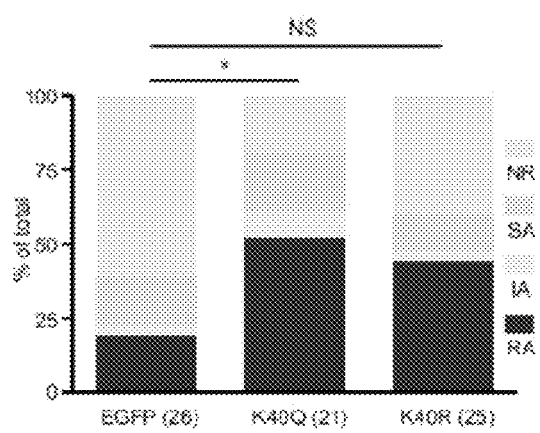
FIG. 3F shows stacked histograms showing the proportions of different mechano-gated currents observed in Atat1$^{cKO}$ sensory neurons transfected with EGFP, α-tubulin$^{K40R}$-IRES-YFP (K40R) or α-tubulin$^{K40Q}$-IRES-YFP (K40Q) cDNA. Transfection of acetylated α-tubulin mimics (K40Q) but not non-acetylatable α-tubulin mutant (K40R) restored mechanosensitivity in Atat1$^{cKO}$ sensory neurons ($\chi^2$ test, EGFP versus K40Q, P<0.05; EGFP versus K40R, P>0.05). The number of neurons recorded is indicated in parentheses in each panel. P<0.01; **P<0.0001; Error bars indicate s.e.m.

The inventors next asked whether the reduction in mechanosensitivity observed in Atat1$^{cKO}$ mice is dependent upon the α-tubulin acetyltransferase activity of αTAT1 by testing if mechanically activated currents could be re-established by expression of exogenous cDNAs. As a positive control the inventors determined that transfection of an Atat1-YFP construct rescued mechanosensitivity in Atat1$^{cKO}$ cultures and that the proportion of RA, IA and SA responses across the DRG returned to control levels (FIG. 3e). The inventors subsequently transfected a catalytically inactive form of αTAT1 that has no acetyltransferase activity but remains functional[24] (termed αTAT1-GGL). Expression of αTAT1-GGL did not restore mechanosensitivity in Atat1$^{cKO}$ neurons, and the inventors observed no difference in the proportion of mechanically activated current types compared to mock eGFP transfection (FIG. 3e). Atat1 has also been demonstrated to acetylate other substrates in addition to α-tubulin[25]. Therefore, to determine whether α-tubulin acetylation underlies the mechanosensory phenotype in Atat1$^{cKO}$ mice, the inventors transfected a K40Q point mutant of α-tubulin that genetically mimics α-tubulin lysine 40 acetylation. Expression of K40Q α-tubulin rescued mechanosensitivity of Atat1$^{cKO}$ DRG neurons to Atat1$^{Control}$ levels, while a charge conserving control mutation (K40R) had no significant effect (FIG. 3f). Collectively these data indicated that the acetyltransferase activity of αTAT1 regulates mechanosensitivity and that acetylated α-tubulin is the likely effector.

Example 4

Microtubule Organization in Peripheral Sensory Neurons

Figure 4A:
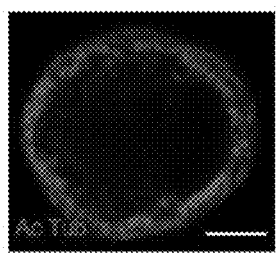
FIG. 4A shows anti-acetylated-α-tubulin staining of Atat1$^{Control}$ cultured DRG cells (corresponding surface plot below). Note the prominent sub-membrane localisation of acetylated tubulin (Scale bar 5 μm).
Figure 4B:
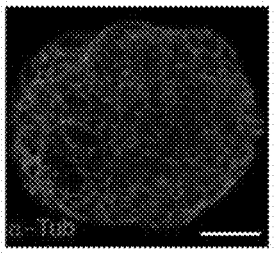
FIG. 4B shows anti α-tubulin staining of Atat1$^{Control}$ cultured DRG cells (Scale bar 5 μm).
Figure 4C:
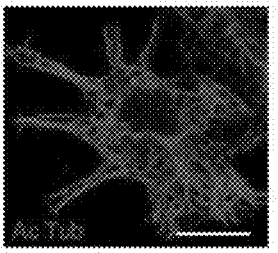
FIG. 4C shows anti-acetylated-α-tubulin staining of Atat1$^{Control}$ MEFs (Scale bar 20 μm). Note the even distribution of acetylated tubulin in this cell type.
Figure 4D:
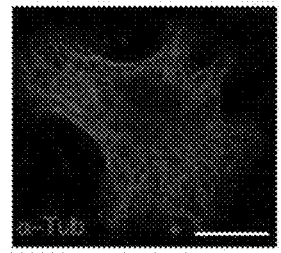
FIG. 4D shows anti α-tubulin staining of Atat1$^{Control}$ MEFs (Scale bar 20 μm).
Figure 4E:
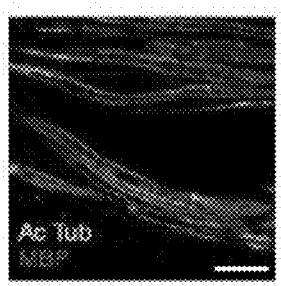
FIG. 4E shows immunohistochemical staining of nerve fibres within the saphenous nerve taken from Atat1$^{Control}$ mice. Anti-acetylated-α-tubulin staining is in green) and myelin basic protein (MBP) is in red (Scale bar 10 μm). Note the sub-membrane localisation of the anti-acetylated tubulin stain.
Figure 4F:
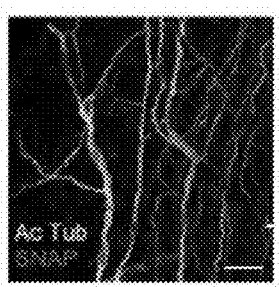
FIG. 4F shows a fluorescent image of free nerve endings in a whole mount cornea preparation from a Avil-Cre::SNAP$^{CaaX}$ mouse. Acetylated tubulin is in green) and membrane bound SNAP staining is in red (Scale bar 30 μm). Note the strong co-localisation of signals.

The inventors investigated a potential structural contribution of acetylated tubulin to mechanosensitivity by examining the distribution of acetylated microtubules in sensory neurons. Strikingly, the inventors observed that acetylated α-tubulin was concentrated in a prominent band directly under the plasma membrane in cultured DRG neurons (FIG. 4a), while total α-tubulin was distributed evenly across the cytoplasm of all cells (FIG. 4b). Importantly, this band was not present in non-mechanosensory cells such as fibroblasts where acetylated α-tubulin was present throughout the microtubule network (FIGS. 4c and d). The inventors further examined the distribution of acetylated α-tubulin in intact preparations of the peripheral nervous system. Again, acetylation was highly enriched under the membrane of axons in the saphenous nerve (FIG. 4e) and also at sensory neuron terminal endings in the cornea (FIG. 4f).

Figure 4G:
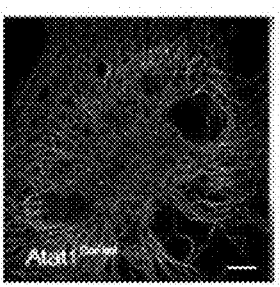
FIG. 4G shows a super-resolution image of an anti α-tubulin staining of Atat1$^{Control}$ cultured DRG colour coded by depth (red close to objective, Scale bar 5 μm).
Figure 4H:
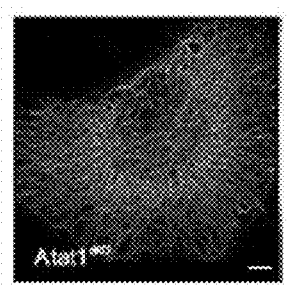
FIG. 4H shows a super-resolution image of an Anti-α tubulin stain in Atat1$^{cKO}$ cultured DRG (Scale bar 5 μm).

The loss of the acetylated α-tubulin sub-membrane band in $Atat1^{cKO}$ mice could potentially impact upon the organization of microtubules in DRG neurons and thereby influence mechanosensitivity. Indeed, it has been recently shown that the arrangement of microtubules is important for mechanosensitivity of hypothalamic osmosensory neurons[26]. Utilizing super-resolution microscopy and automated analysis of α-tubulin distribution, the inventors were unable however to detect any difference in the spatial arrangement of microtubules in sensory neurons from $Atat1^{Control}$ and $Atat1^{cKO}$ mice (FIGS. 4g and h). Furthermore, the organization of the actin cytoskeleton also appeared unaltered in $Atat1^{cKO}$ mice.

Figure 4I:
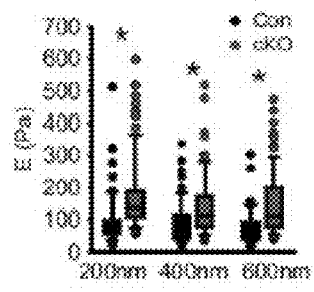
FIG. 4I is a graphical summary of AFM analysis showing the pressure required to indent the membrane to 200, 400 and 600 nm respectively, using a blunt ended cantilever in cultured DRG taken from Atat1$^{Control}$ and Atat1$^{cKO}$ mice. A significantly higher pressure is required to indent the membranes of Atat1$^{cKO}$ neurons over Atat1$^{Control}$ cells (Mann-Whitney test, P<0.01).
Figure 4J:
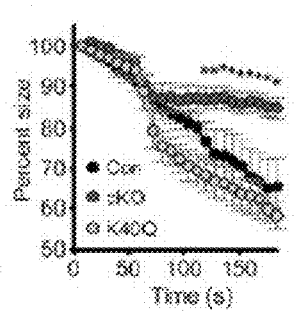
FIG. 4J is a graph showing the relative shrinkage of axonal outgrowths from Atat1$^{Control}$ and Atat1$^{cKO}$ DRG loaded with calcein (2 μM) in response to a hyperosmotic shock over time. Deletion of Atat1 leads to a significant decrease in the percentage shrinking of axons relative to control samples (ANOVA on ranks, multiple comparison Dunn's Method, P<0.05).

What then is the function of the acetylated α-tubulin band, and how does it impact upon mechanosensitivity across the range of mechanoreceptors in the skin? One possibility is that it sets the rigidity of cells thereby influencing the amount of force required to displace the plasma membrane and activate mechanosensitive channels. The inventors explored this by directly measuring membrane elasticity using atomic force microscopy. In DRG neurons from $Atat1^{cKO}$ mice the inventors observed that cellular stiffness was significantly higher across a range of indentations extending from displacements that perturbed mainly the membrane (200 nm) to those that deformed the underlying cytoskeleton (600 nm) (FIG. 4i). Thus higher forces are required to indent sensory neurons from $Atat1^{cKO}$ mice than $Atat1^{Control}$ mice. The inventors investigated this further by assaying the sensitivity of neurons to hyperosmotic induced shrinkage. In the absence of Atat1, sensory neuron axons displayed less shrinkage than their control counterparts, an effect that could be rescued by expression of the acetylation mimicking mutation α-tubulin K40Q (FIG. 4j).

Figure 4K:
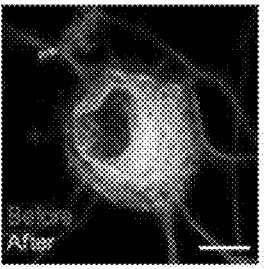
FIG. 4K is an image from a cultured DRG cell showing an overlay of C8 SIR tubulin labelled microtubules before (purple) and after (green) hyperosmotic shock. Note the clear compression of the microtubule cytoskeleton after shrinking (Scale bar 10 μm).
Figure 4L:
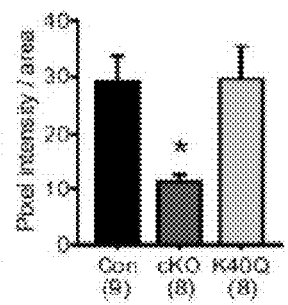
FIG. 4L is a bar chart summarising osmotically induced microtubule compression in DRG neurons from Atat1$^{Control}$, Atat1$^{cKO}$, and Atat1$^{cKO}$ neurons transfected with tubulin-K40Q. There is significantly less compression in Atat1$^{cKO}$ than Atat1$^{Control}$ neurons, which is rescued by transfection of tubulin-K40Q (ANOVA on ranks, multiple comparison Dunn's Method, P<0.05). Error bars indicate s.e.m.

Finally the inventors examined how the microtubule cytoskeleton responds to compression induced by osmotic pressure. Using a novel tubulin labelling fluorescent dye the inventors were able to resolve individual microtubule bundles in live imaging experiments. Strikingly, in DRG neurons from $Atat1^{cKO}$ mice the inventors observed significantly reduced microtubule displacement upon application of hyperosmotic solutions (FIGS. 4k and 4l), again supporting the premise that in the absence of α-tubulin acetylation sensory neurons are more resistant to mechanical deformation.

References

1 Abraira, V. E. & Ginty, D. D. The sensory neurons of touch. *Neuron* 79, 618-639, doi:10.1016/j.neuron.2013.07.051 (2013).
2 Maksimovic, S. et al. Epidermal Merkel cells are mechanosensory cells that tune mammalian touch receptors. *Nature* 509, 617-621, doi:10.1038/nature13250 (2014).
3 Ranade, S. S. et al. Piezo2 is the major transducer of mechanical forces for touch sensation in mice. *Nature* 516, 121-125, doi:10.1038/nature13980 (2014).
4 Woo, S. H. et al. Piezo2 is required for Merkel-cell mechanotransduction. *Nature* 509, 622-626, doi:10.1038/nature13251 (2014).
5 Qi, Y. et al. Membrane stiffening by STOML3 facilitates mechanosensation in sensory neurons. *Nature communications* 6, 8512, doi:10.1038/ncomms9512 (2015).
6 Delmas, P., Hao, J. & Rodat-Despoix, L. Molecular mechanisms of mechanotransduction in mammalian sensory neurons. *Nat Rev Neurosci* 12, 139-153, doi:10.1038/nrn2993 (2011).
7 Sukharev, S. Purification of the small mechanosensitive channel of *Escherichia coli* (MscS): the subunit structure, conduction, and gating characteristics in liposomes. *Biophys J* 83, 290-298, doi:10.1016/S0006-3495(02)75169-2 (2002).
8 Brohawn, S. G., Su, Z. & MacKinnon, R. Mechanosensitivity is mediated directly by the lipid membrane in TRAAK and TREK1 K+ channels. *Proc Natl Acad Sci USA* 111, 3614-3619, doi:10.1073/pnas.1320768111 (2014).
9 Krieg, M., Dunn, A. R. & Goodman, M. B. Mechanical systems biology of *C. elegans* touch sensation. *Bioessays* 37, 335-344, doi:10.1002/bies.201400154 (2015).
10 Zhang, W. et al. Ankyrin Repeats Convey Force to Gate the NOMPC Mechanotransduction Channel. *Cell* 162, 1391-1403, doi:10.1016/j.cell.2015.08.024.
11 Krieg, M., Dunn, A. R. & Goodman, M. B. Mechanical control of the sense of touch by beta-spectrin. *Nat Cell Biol* 16, 224-233, doi:10.1038/ncb2915 (2014).
12 Chalfie, M. & Thomson, J. N. Organization of neuronal microtubules in the nematode *Caenorhabditis elegans*. *J Cell Biol* 82, 278-289 (1979).
13 Bounoutas, A., O'Hagan, R. & Chalfie, M. The multipurpose 15-protofilament microtubules in *C. elegans* have specific roles in mechanosensation. *Current biology: CB* 19, 1362-1367, doi:10.1016/j.cub.2009.06.036 (2009).
14 Zhang, Y. et al. Identification of genes expressed in *C. elegans* touch receptor neurons. *Nature* 418, 331-335, doi:10.1038/nature00891
15 Topalidou, I. et al. Genetically Separable Functions of the MEC-17 Tubulin Acetyltransferase Affect Microtubule Organization. *Current biology:CB*, doi:10.1016/j.cub.2012.03.066 (2012).
16 Cueva, J. G., Hsin, J., Huang, K. C. & Goodman, M. B. Posttranslational Acetylation of alpha-Tubulin Constrains Protofilament Number in Native Microtubules. *Current biology*: CB, doi:10.1016/j.cub.2012.05.012 (2012).
17 Kalebic, N. et al. Tubulin acetyltransferase alphaTAT1 destabilizes microtubules independently of its acetylation activity. *Mol Cell Biol* 33, 1114-1123, doi:10.1128/MCB.01044-12 (2013).
18 Kalebic, N. et al. alphaTAT1 is the major alpha-tubulin acetyltransferase in mice. *Nature communications* 4, 1962, doi:10.1038/ncomms2962 (2013).
19 Zurborg, S. et al. Generation and characterization of an Advillin-Cre driver mouse line. *Molecular pain* 7, 66, doi:10.1186/1744-8069-7-66 (2011).
20 Garrison, S. R., Dietrich, A. & Stucky, C. L. TRPC1 contributes to light-touch sensation and mechanical responses in low-threshold cutaneous sensory neurons. *J Neurophysiol* 107, 913-922, doi:10.1152/jn.00658.2011 (2012).
21 Rugiero, F., Drew, L. J. & Wood, J. N. Kinetic properties of mechanically activated currents in spinal sensory neurons. *J Physiol* 588, 301-314, doi:10.1113/jphysiol.2009.182360 (2010).

22 Sung, K., Maloney, M. T., Yang, J. & Wu, C. A novel method for producing mono-biotinylated, biologically active neurotrophic factors: an essential reagent for single molecule study of axonal transport. *Journal of neuroscience methods* 200, 121-128, doi:10.1016/j.jneumeth.2011.06.020 (2011).

23 Hu, J. & Lewin, G. R. Mechanosensitive currents in the neurites of cultured mouse sensory neurones. *The Journal of physiology* 577, 815-828, doi:10.1113/jphysiol.2006.117648 (2006).

24 Kalebic, N. et al. The Tubulin Acetyltransferase alphaTAT1 Destabilizes Microtubules Independently of its Acetylation Activity. *Mol Cell Biol*, doi:10.1128/MCB.01044-12 (2012).

25 Castro-Castro, A., Janke, C., Montagnac, G., Paul-Gilloteaux, P. & Chavrier, P. ATAT1/MEC-17 acetyltransferase and HDAC6 deacetylase control a balance of acetylation of alpha-tubulin and cortactin and regulate MT1-MMP trafficking and breast tumor cell invasion. *Eur J Cell Biol* 91, 950-960, doi:10.1016/j.ejcb.2012.07.001 (2012).

26 Prager-Khoutorsky, M., Khoutorsky, A. & Bourque, C. W. Unique interweaved microtubule scaffold mediates osmosensory transduction via physical interaction with TRPV1. *Neuron* 83, 866-878, doi:10.1016/j.neuron.2014.07.023 (2014).

27 Wetzel, C. et al. A stomatin-domain protein essential for touch sensation in the mouse. *Nature* 445, 206-209 (2007).

28 Yang, G. et al. Genetic targeting of chemical indicators in vivo. *Nat Methods* 12, 137-139, doi:10.1038/nmeth.3207 (2015).

29 Carpenter, A. E. et al. CellProfiler: image analysis software for identifying and quantifying cell phenotypes. *Genome biology* 7, R100, doi:10.1186/gb-2006-7-10-r100 (2006).

30 Rotsch, C., Jacobson, K. & Radmacher, M. Dimensional and mechanical dynamics of active and stable edges in motile fibroblasts investigated by using atomic force microscopy. *Proc Natl Acad Sci USA* 96, 921-926 (1999).

The invention claimed is:

1. A method for reducing expression of ATAT1 in a subject experiencing mechanical pain mediated by sensory neurons, the method comprising:
    administering to the subject an effective amount of a nucleic acid that is capable of reducing expression of ATAT1;
    wherein the mechanical pain is selected from the group consisting of:
        inflammatory pain, acute mechanical pain, chronic mechanical pain, mechanical hyperalgesia, mechanical allodynia, visceral pain, and labor pain.

2. The method of claim 1, wherein the acute mechanical pain is due to physical trauma selected from soft tissue damage, infection and inflammation.

3. The method of claim 1, wherein the acute mechanical pain is selected from pain due to surgery, cuts, bruises, fractured or broken bones, hemorrhoids, intestinal gas, dyspepsia and dental pain.

4. The method of claim 1, wherein the chronic mechanical pain is a pain that lasts longer than 1 month or beyond the resolution of an acute tissue injury or is recurring or is associated with tissue injury and/or chronic diseases that are expected to continue or progress.

5. The method of claim 1, wherein the chronic mechanical pain is selected from pain due to inflammatory disease, cancer, arthritis, chronic wounds, cardiovascular incidents, spinal cord disorders, central nervous system disorder, recovery from surgery, and neuropathy.

6. The method of claim 1, wherein the chronic mechanical pain is selected from pain due to osteoarthritis, rheumatoid arthritis, fibromyalgia, meralgia paresthetica, back pain, angina, carpel tunnel syndrome, menstruation, and hemorrhoids.

7. The method of claim 1, wherein the visceral pain is selected from pain due to menstruation, inflammation, cancer, dyspepsia, and intestinal gas.

8. The method of claim 1, wherein the nucleic acid is capable of reducing expression of ATAT1 through RNA interference.

9. The method of claim 8, wherein the nucleic acid encodes a shRNA.

10. The method of claim 8, wherein the nucleic acid encodes a siRNA.

11. The method of claim 1, wherein mechanical pain is reduced.

12. A method for reducing pain in a subject experiencing mechanical pain mediated by sensory neurons, the method comprising:
    administering to the subject an effective amount of a nucleic acid that is capable of reducing expression of ATAT1;
    wherein the mechanical pain is selected from the group consisting of:
        inflammatory pain, acute mechanical pain, chronic mechanical pain, mechanical hyperalgesia, mechanical allodynia, visceral pain, and labor pain.

13. The method of claim 12, wherein the acute mechanical pain is due to physical trauma selected from soft tissue damage, infection, and inflammation.

14. The method of claim 12, wherein the acute mechanical pain is selected from pain due to surgery, cuts, bruises, fractured or broken bones, hemorrhoids, intestinal gas, dyspepsia and dental pain.

15. The method of claim 12, wherein the chronic mechanical pain is a pain that lasts longer than 1 month or beyond the resolution of an acute tissue injury or is recurring or is associated with tissue injury and/or chronic diseases that are expected to continue or progress.

16. The method of claim 12, wherein the chronic mechanical pain is selected from pain due to inflammatory disease, cancer, arthritis, chronic wounds, cardiovascular incidents, spinal cord disorders, central nervous system disorder, recovery from surgery, and neuropathy.

17. The method of claim 12, wherein the chronic mechanical pain is selected from pain due to osteoarthritis, rheumatoid arthritis, fibromyalgia, meralgia paresthetica, back pain, angina, carpel tunnel syndrome, menstruation, and hemorrhoids.

18. The method of claim 12, wherein the visceral pain is selected from pain due to menstruation, inflammation, cancer, dyspepsia, and intestinal gas.

19. The method of claim 12, wherein the nucleic acid is capable of reducing expression of ATAT1 through RNA interference.

20. The method of claim 19, wherein the nucleic acid encodes a shRNA.

21. The method of claim 19, wherein the nucleic acid encodes a siRNA.

22. The method of claim 12, wherein mechanical pain is reduced.

* * * * *